(12) United States Patent
Morrow et al.

(10) Patent No.: US 7,398,160 B2
(45) Date of Patent: Jul. 8, 2008

(54) GAS ENERGY METER FOR INFERENTIAL DETERMINATION OF THERMOPHYSICAL PROPERTIES OF A GAS MIXTURE AT MULTIPLE STATES OF THE GAS

(75) Inventors: Thomas B. Morrow, San Antonio, TX (US); Eric Kelner, San Antonio, TX (US); Thomas E. Owen, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 81 days.

(21) Appl. No.: 11/171,977

(22) Filed: Jun. 30, 2005

(65) Prior Publication Data

US 2006/0064254 A1 Mar. 23, 2006

Related U.S. Application Data

(60) Provisional application No. 60/584,089, filed on Jun. 30, 2004.

(51) Int. Cl.
*G06F 19/00* (2006.01)
(52) U.S. Cl. ....................................................... 702/24
(58) Field of Classification Search .................. 702/24, 702/23, 23.2; 73/23.2
See application file for complete search history.

(56) References Cited

U.S. PATENT DOCUMENTS

| | | | |
|---|---|---|---|
| 4,489,592 A | 12/1984 | Pacanowski et al. | 73/24.05 |
| 4,596,133 A | 6/1986 | Smalling et al. | 73/24 |
| 5,285,675 A | 2/1994 | Colgate et al. | 73/23.2 |
| 5,311,447 A | 5/1994 | Bonne | 702/50 |
| 5,486,107 A | 1/1996 | Bonne | 431/12 |
| 5,537,854 A | 7/1996 | Phillips et al. | 73/24.01 |
| 5,932,793 A | 8/1999 | Dayton et al. | 73/24.05 |
| 6,047,589 A | 4/2000 | Hammond et al. | 73/24.01 |
| 6,065,328 A | 5/2000 | Dayton et al. | 73/25.01 |
| 6,076,392 A | 6/2000 | Drzewiecki | 73/23.2 |
| 6,209,387 B1 | 4/2001 | Savidge | 73/24.05 |
| 6,244,097 B1 | 6/2001 | Schley et al. | 73/23.2 |
| 6,286,360 B1 | 9/2001 | Drzewiecki | 73/24.01 |
| 6,604,051 B1 | 8/2003 | Morrow et al. | 702/24 |

(Continued)

FOREIGN PATENT DOCUMENTS

DE 19823193 11/1999

(Continued)

OTHER PUBLICATIONS

International Preliminary Examination Report PCT/US01/12217, Jul. 8, 2002.

(Continued)

*Primary Examiner*—Tung S Lau
(74) *Attorney, Agent, or Firm*—Baker Botts LLP

(57) ABSTRACT

A gas energy meter that acquires the data and performs the processing for an inferential determination of one or more gas properties, such as heating value, molecular weight, or density. The meter has a sensor module that acquires temperature, pressure, CO2, and speed of sound data. Data is acquired at two different states of the gas, which eliminates the need to determine the concentration of nitrogen in the gas. A processing module receives this data and uses it to perform a "two-state" inferential algorithm.

19 Claims, 7 Drawing Sheets

U.S. PATENT DOCUMENTS

| | | | |
|---|---|---|---|
| 6,704,660 B2 | 3/2004 | Morrow et al. | 702/24 |
| 6,754,592 B2 | 6/2004 | Morrow et al. | 702/27 |
| 6,804,610 B2 | 10/2004 | Morrow et al. | 702/24 |
| 2003/0114992 A1* | 6/2003 | Morrow et al. | 702/23 |

FOREIGN PATENT DOCUMENTS

| | | |
|---|---|---|
| EP | 0939317 | 9/1999 |
| EP | 0959354 | 11/1999 |
| EP | 1063525 | 12/2000 |
| WO | 9308457 | 4/1993 |
| WO | 9910740 | 3/1999 |

OTHER PUBLICATIONS

International Search Report PCT/US 01/12217, Nov. 13, 2001.

* cited by examiner

DATA RECORDING AND PROCESSING SEQUENCE

US 7,398,160 B2

GAS ENERGY METER FOR INFERENTIAL DETERMINATION OF THERMOPHYSICAL PROPERTIES OF A GAS MIXTURE AT MULTIPLE STATES OF THE GAS

RELATED APPLICATION

This application claims priority to U.S. provisional patent application No. 60/584,089, entitled "Gas Energy Meter for Inferential Determination of Thermophysical Properties of a Gas Mixture at Multiple States of the Gas," filed on Jun. 30, 2004.

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

TECHNICAL FIELD OF THE INVENTION

This invention relates to devices for measuring thermophysical properties (such as heating value) of gas mixtures.

BACKGROUND OF THE INVENTION

Traditionally, the natural gas industry has relied on gas chromatography to analyze the energy content or heating value of natural gas. The cost of installing, operating, and maintaining gas chromatographs is high.

As an alternative to gas chromatography, the following patents describe a new method for determining natural gas properties, such as heating value, molecular weight, and density: U.S. Pat. No. 6,604,051, entitled "System and Method to Determine Thermophysical Properties of a Multi-Component Gas", U.S. Pat. No. 6,704,660, entitled "System and Method to Determine Thermophysical Properties of a Multi-Component Gas at Arbitrary Temperature and Pressure", U.S. Pat. No. 6,850,847, entitled "Device for Determining Thermophysical Properties of a Multi-Component Gas at Arbitrary Temperature and Pressure, and U.S. patent application Ser. No. 10/770,768, entitled "Inferential Determination of Various Properties of Multi-Component Gases". The method is based on the idea that natural gas properties can be inferentially determined from model equations having coefficients derived from a set of reference gases. More specifically, relatively simple measurements of the gas temperature, pressure, and sound speed, as well as the diluent concentrations for nitrogen and carbon dioxide are all that are required as inputs for the inferential algorithm.

This new technology provides substantial cost savings, with no appreciable loss in measurement precision, when used in place of conventional gas chromatographs. Also, because of its expected cost effectiveness, this technology can be deployed at many field measurement sites where gas chromatography is not economically viable. Although its primary application is expected to be for natural gas pipeline measurements, the inferential algorithm is useful for any gas mixture containing carbon dioxide and/or nitrogen diluents.

As stated above, one of the inputs for the inferential algorithm is the nitrogen concentration of the gas mixture. No simple, accurate and inexpensive method for determining nitrogen concentration in natural gas currently exists. However, instead of attempting to directly measure nitrogen, alternative methods have been developed for inferential measurement. For example, U.S. Pat. No. 6,804,610, entitled "Indirect Measurement of Nitrogen in a Multi-Component Gas by Measuring the Speed of Sound at Two States of the Gas", describes a method of inferentially determining nitrogen concentration in a natural gas mixture by using the above-described inferential algorithm, applied at two different thermodynamic states. The technique is referred to herein as the "two-state" inferential gas analysis algorithm.

DETAILED DESCRIPTION OF THE INVENTION

Figure 1:
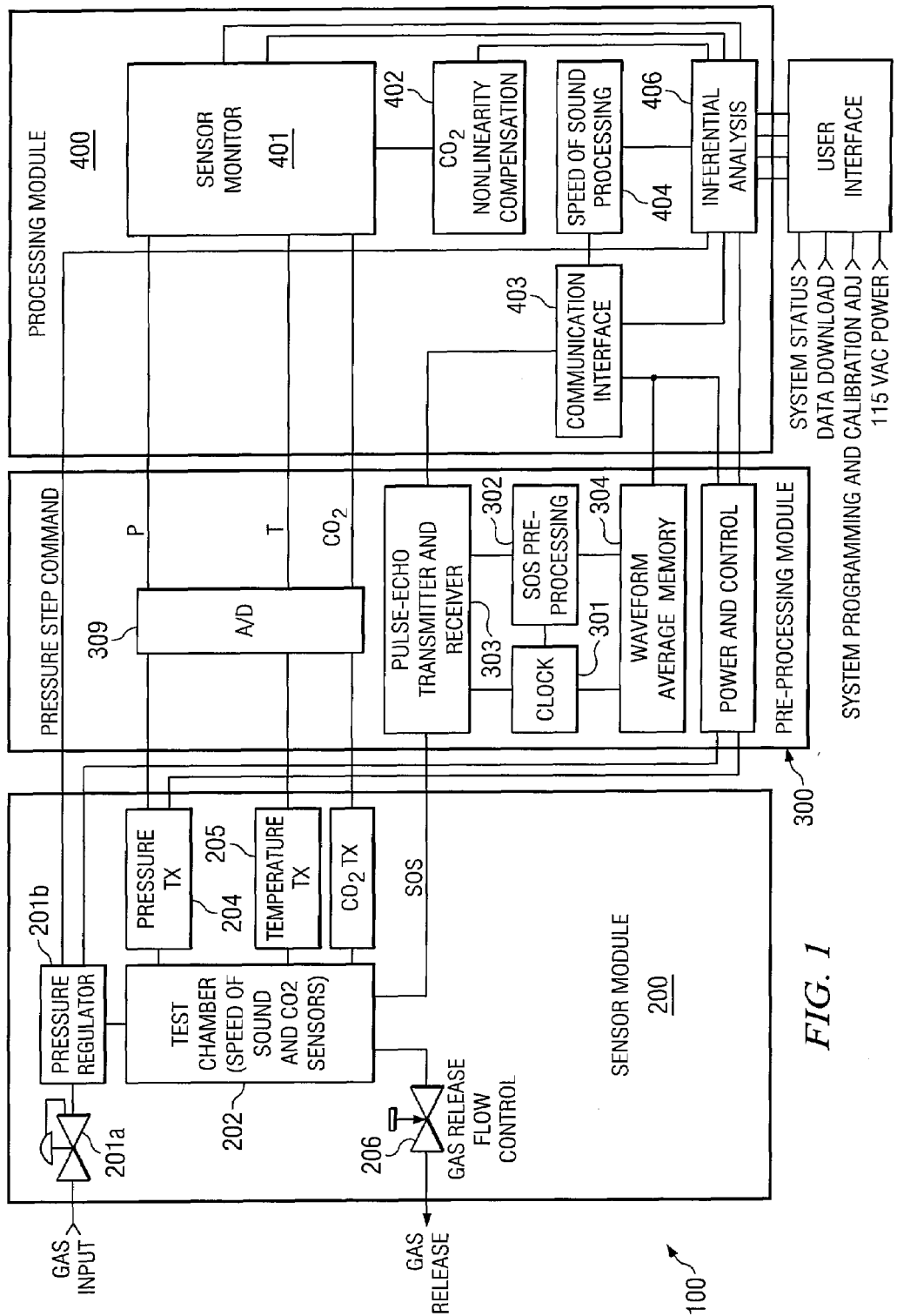
FIG. 1 illustrates a gas energy meter system in accordance with the invention.

FIG. 1 illustrates a gas energy meter 100 in accordance with the invention. Energy meter 100 may be used to implement the "two-state" inferential gas analysis algorithm described in the Background. That is, it may be used to implement an inferential gas property analysis algorithm by incorporating inferential determination of nitrogen. Various gas properties that may be determined using meter 100 include heating values, molecular weight, and density values.

A sensor module 200 acquires signals representing input data for the inferential energy analysis algorithm. Pre-processing module 300 receives these signals, and provides signal conditioning and pre-processing. A data processing module 400 performs various calculations, including speed of sound calculations and the inferential energy analysis algorithm.

Each of these modules is explained in further detail below. It should be understood that the partitioning of various functions into the three modules of FIG. 1 is somewhat arbitrary, with the sensor elements being separated from the data processing elements and the pre-processing elements being further separated from the more intensive processing elements. One advantage of this modularization is to facilitate in situ placement of the sensor module 200 and remote location of modules 300 and 400. However, it is entirely possible that either or both modules 300 and 400 could be integrated with module 200 and housed and installed in situ. It is further possible that the various elements of modules 300 and 400 could be placed in either of these modules, or that all elements could be integrated into a single data processing module. Features of the modular design of FIG. 1, would be modified accordingly, such as the elimination of temperature and pressure signal transmitters in the sensor module 200.

Gas Sensor Module

Figure 2:
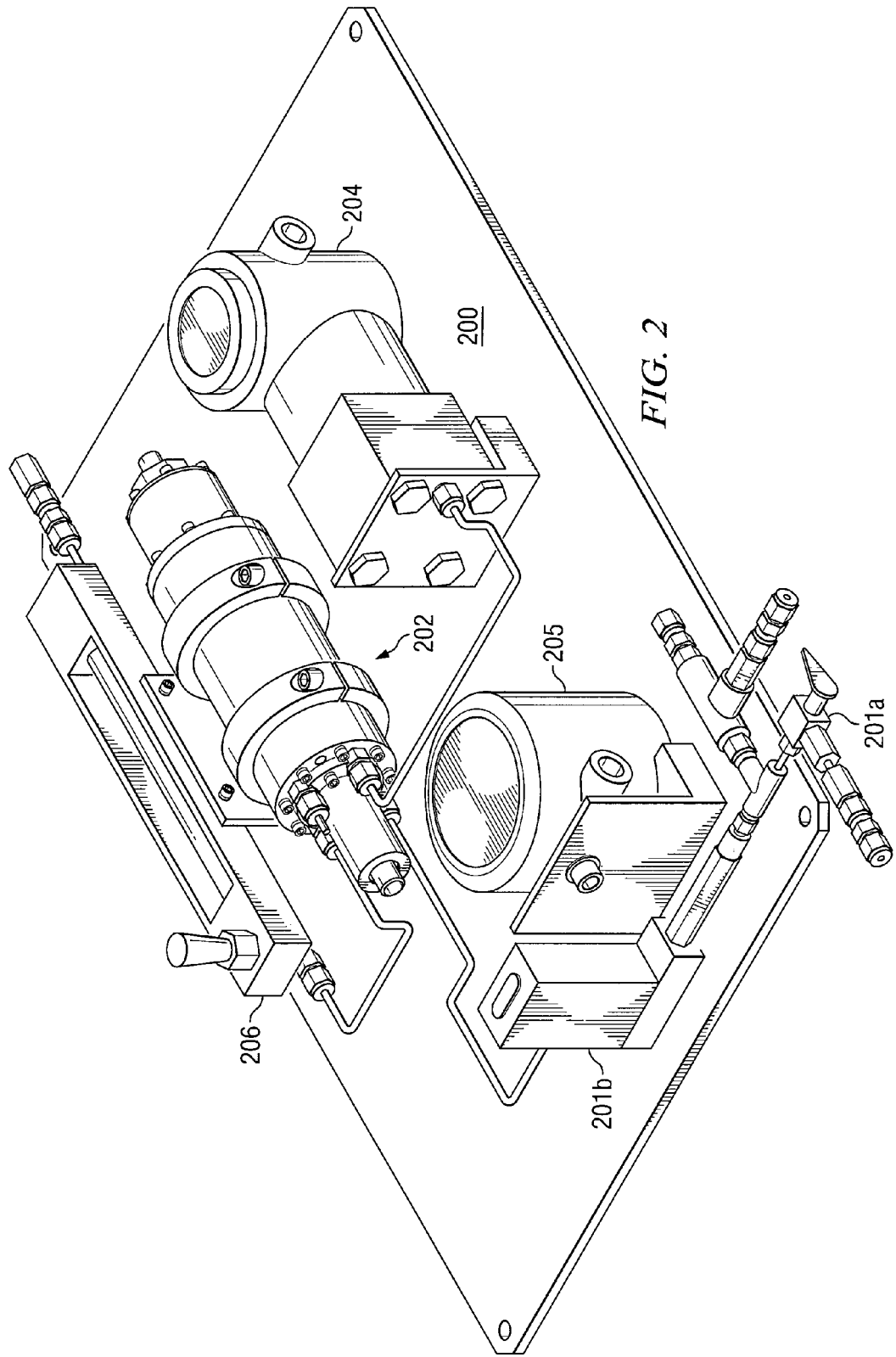
FIG. 2 illustrates the gas sensor module of FIG. 1.

FIG. 2 illustrates an example of one implementation of the gas sensor module 200 of FIG. 1. The primary function of sensor module 200 is to acquire speed of sound (SOS), carbon dioxide (CO2), pressure (P), and temperature (T) measurements and to deliver output signals representing these measurements to module 300.

Referring to both FIGS. 1 and 2, gas sensor module 200 comprises an gas input valve 201a, gas pressure regulator 201b, test chamber 202, pressure signal transmitter 204, temperature signal transmitter 205, carbon dioxide signal transmitter 206, and gas release valve 206.

Pressure regulator 201b is an electronically controlled pressure regulator. It pressurizes the gas within test chamber 202 to a desired pressure. For example, pressure regulator 201b may permit the gas to be pressurized to any specified pressure within a range of 0-150 psi. This permits test chamber 202 to measure the speed of sound in the test gas at two or more specified pressure states. In the example of this description, speed of sound is measured at a low-pressure state of 70 psia and a high-pressure state of 100 psia.

Test chamber 202 is an integrated speed of sound (SOS) and carbon dioxide (CO2) measurement device. In other words, a feature of test chamber 202 is that it integrates the functions of speed of sound measurement and CO2 concentration sensing into a single unit. This permits the use of a single temperature sensor and a single pressure sensor, and permits the assumption that temperature (T) and pressure (P) are the same for the SOS and CO2 measurements. In other embodiments, separate SOS and CO2 sensors could be used. Test chamber 202 is described in further detail in connection with FIGS. 3 and 4.

Pressure transmitter 204 and temperature transmitter 205 provide electronic circuitry for delivering pressure and temperature signals to pre-processing module 300. In the example of this description, the pressure and temperature sensors 204 and 205 provide continuous analog current readout signals. As explained below in connection with FIGS. 3 and 4, the temperature and pressure measurements represent the pressure and temperature within chamber 202. CO2 transmitter 206 delivers a signal representing the CO2 concentration in the gas mixture.

A feature of module 100 is that it need not include a nitrogen sensor (or equivalently, a sensor for any second diluent in the gas mixture). Instead, nitrogen content may be calculated by module 400, using the measurement data acquired by module 200. As stated in the Background, methods have been developed to inferentially determine nitrogen concentration for a broad range of gas compositions, temperatures, and pressures. Further, a "two-state" inferential gas analysis permits a desired gas property to be inferentially calculated without direct measurement of nitrogen.

Module 200 may designed and housed to be placed "in situ", that is, inserted into a gas pipeline. For example, module 200 could be designed as a cartridge-type device. Alternatively, module 200 may be used as a retrofit device with an existing pipeline, installed as near as practical to the gas pipeline to be monitored, using small-bore connecting tubing.

To operate at the high-pressure test state of 150 psia, the inlet source gas pressure is approximately 175 psia for proper pre-regulation of the test pressure. For this purpose, the pipeline source pressure should be at least 200 psia or higher. The gas flow rate released to atmosphere is controlled by valve 207 to approximately 30 cm$^3$/min at the low-pressure test state of 70 psia. The gas release flow at the high-pressure state will be approximately 100 cm$^3$/min. When the module 200 is operated at 45 seconds per pressure test state as described in the example of this description, a volumetric turnover of gas in the test chamber 202 occurs within a 10 minute time interval.

Figure 3:
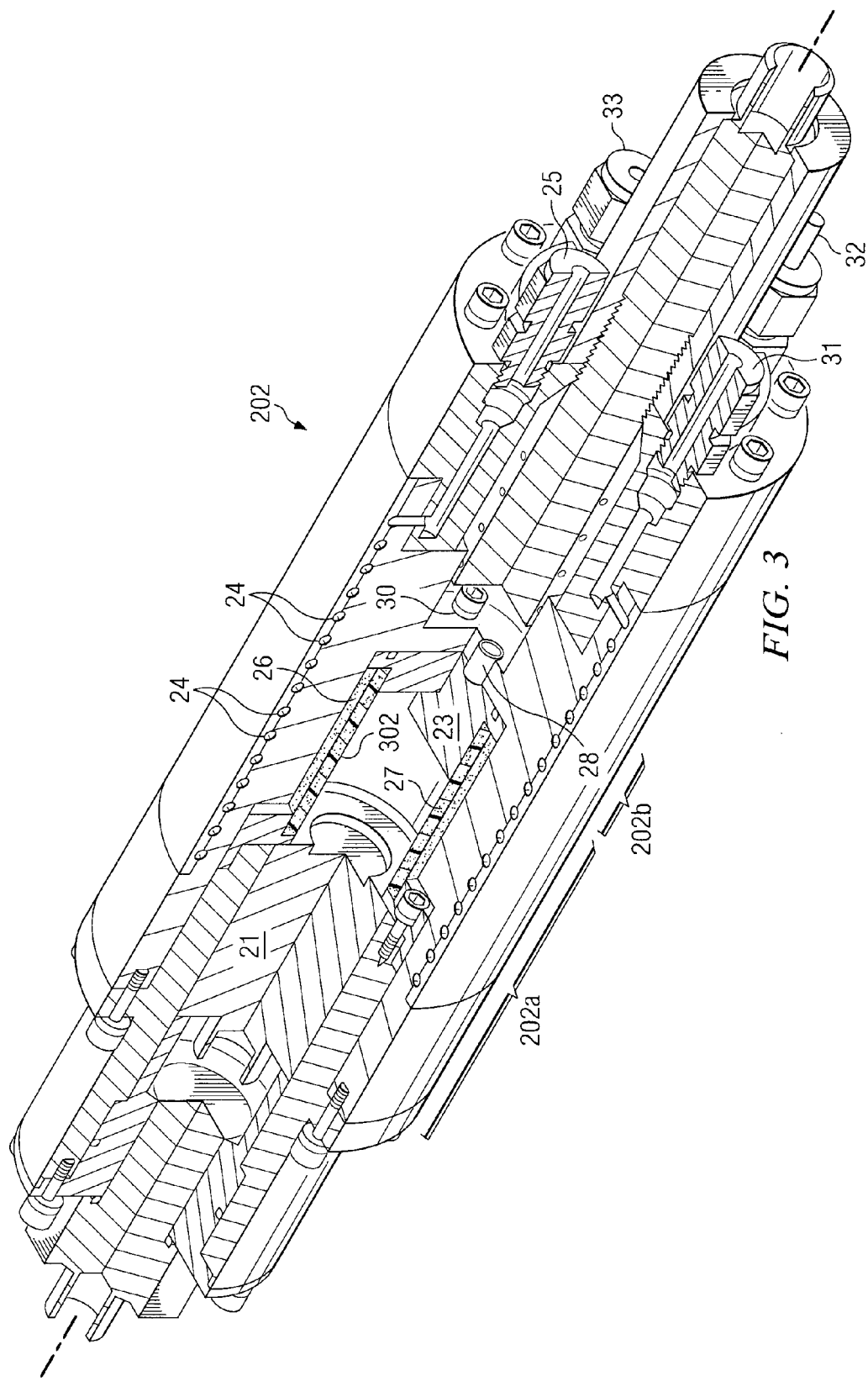
FIG. 3 is a cut-away illustration of the speed of sound (SOS) and carbon dioxide (CO2) test chamber of FIGS. 1 and 2.
Figure 4:
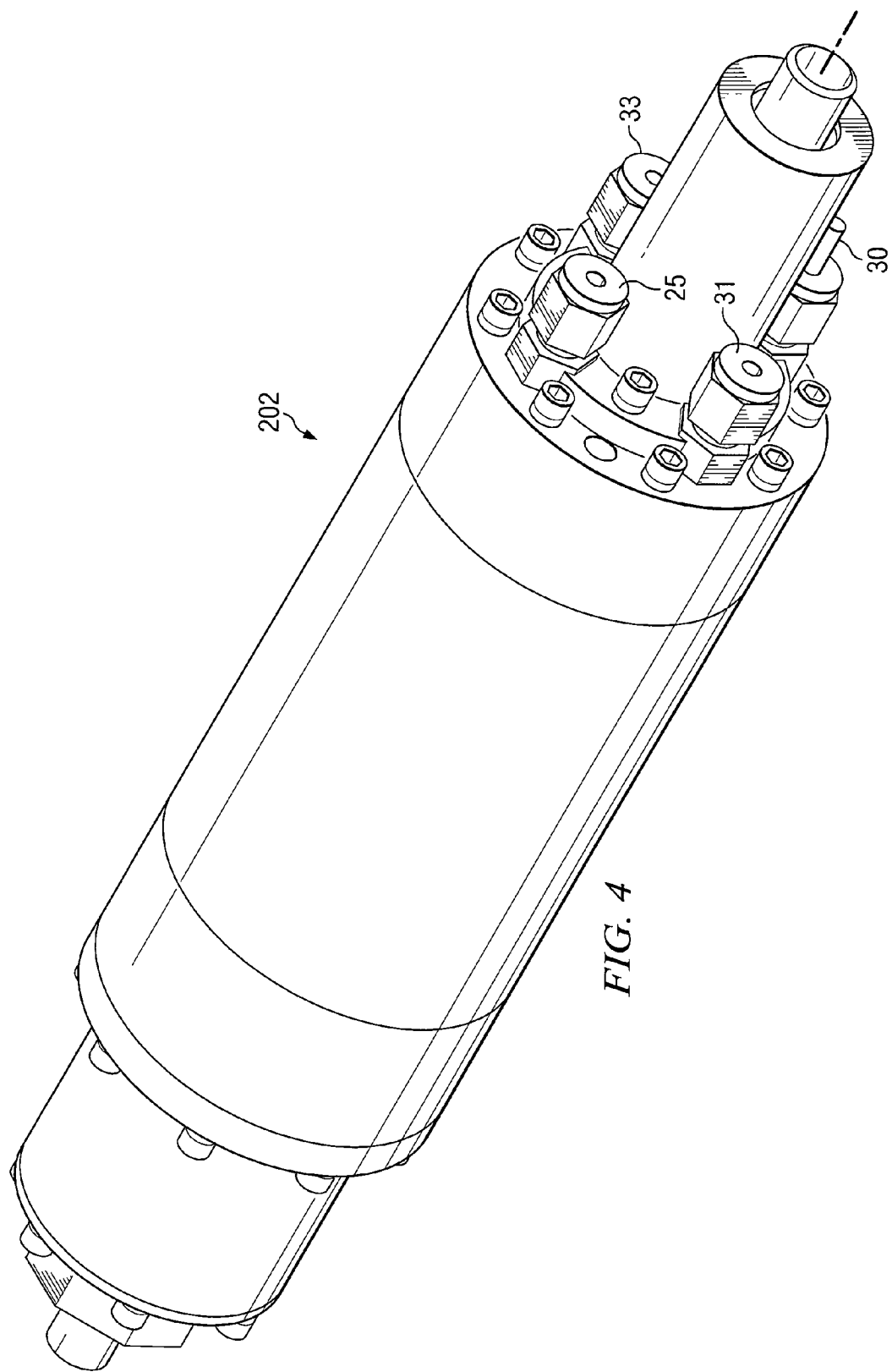
FIG. 4 is a perspective view of the test chamber of FIG. 3, showing its inputs and outputs.

FIG. 3 is a cut-away illustration of test chamber 202. FIG. 4 is a perspective view of test chamber 202, showing its inputs and outputs. In general, sensor 202 is cylindrical in shape, having a common axis of assembly.

As explained below, test chamber 202 serves as a gas flow heat sink to equilibrate a continuous flow of the test gas to the ambient temperature of module 200. This facilitates precision measurements of the gas temperature, pressure, carbon dioxide concentration, and ultrasonic SOS waveforms at two different test pressures. Thus, in the example of this description, the two measurement states of the "two-state" method are achieved by varying pressure and maintaining temperature.

The first portion of test chamber 202 is a speed of sound sensor 202a, which comprises an ultrasonic transducer 21, SOS measurement channel 22, and two-reflector target 23. In operation, speed of sound sensor 202a uses ultrasonic pulse-echo reflections from two faces of target 303, which are separated by a known distance. The parameter of interest is the difference in the two-way travel time between the two detected reflections, which is governed by the known distance between the two reflecting faces of target 23. The time difference is derived by computing the cross correlation between the two reflections in an output waveform.

The temperature of the test gas is equilibrated to the temperature of the test chamber 202 prior to entering the speed of sound measurement channel 22. To this end, a helical inlet flow tube 24 spirals around the mid-diameter of chamber 202, along a portion of the length of the chamber 202. In this manner, the thermal mass of the test chamber 202 is used as a heat sink.

One example of how helical flow tube 24 may be implemented is to construct it in the form of a groove, somewhat similar to a screw thread, machined into an outer surface of test chamber 202. This groove is then closed by an outer sleeve 25 to form the helical flow channel 24. The outer sleeve 25 is sealed at the chamber end plates so that the entire internal volume of the chamber 202, including the helical flow channel 24, retains the gas pressure. One end plate is arranged to accept gas flowing into a gas inlet port 25, and, through an internal path, directs it into the upstream end of the helical flow tube 24. The gas then flows through the helical flow tube 24, winding around the mid-diameter of chamber 202 until it reaches an output end of the flow tube 24.

The flow rate of the gas is adjusted such that all gas within flow channel 24 contacts the sides of the flow channel 24. During this time period, the gas gives up or accepts heat energy from the chamber 202 so as to equilibrate to the same temperature of the chamber 202 by the time it exits flow tube 24.

Upon exit from flow tube 24, an internal path directs the gas into an annular space 26, where it travels freely between an inner wall of the chamber 202 and a porous sleeve 27, concentric with the chamber 202. It diffuses through sleeve 27 into the speed of sound measurement channel 22. By traveling through the helical flow channel 24 and diffusing uniformly through the porous sleeve 27, the gas is assured to have the same temperature as the test chamber 202 and its temperature throughout the measurement channel 22 is uniform.

Ultrasonic transducer 21 is located in the inner space of chamber 202 at a first end of measurement channel 22. Transducer 21 emits a short duration sound wave pulse, whose time of travel between the reflecting surfaces is to be measured. An example of a suitable transducer is a pulse-echo transducer having a resonance frequency of approximately 1 MHz, which generates oscillatory sound wave pulses having a time duration of approximately 4 μsec and a pulse repetition rate of 40 pulses/sec. Transducer 21 may have a manually adjustable or automatic gain control, adjusted to accommodate changes in ultrasonic signal amplitude caused by extreme temperature effects or variations in the gas mixture compositions. Transducer 21 is operated for only a few seconds near the end of each pressure state test interval.

The reflector target 23 may be made from a single piece of material to provide the two reflecting surfaces accurately separated by a precisely known distance along the axial length of the test chamber 202. These reflecting surfaces may be made physically identical in all respects, of a material that has a low coefficient of thermal expansion. Two specific examples of suitable materials for the target 23 are Invar® and Super Invar®. A suitable construction of the target 23 is two semi-circular faces of a cylinder, such that the semicircular faces are oriented parallel to the face of transducer.

Further details about a suitable speed of sound sensor, which may be used to implement sensor 202a, are set out in U.S. Pat. No. 6,823,716, entitled "Device for Precision Measurement of Speed of Sound in a Gas", incorporated by reference herein.

The lower portion of test chamber 202 comprises a CO2 sensor 202b. A gas passageway 28 delivers gas from the target area of the SOS sensor 202a into a chamber 29, where CO2 is sensed. CO2 sensing can be accomplished with an infrared sensor 30, using known infrared sensing techniques. Examples of suitable CO2 sensing techniques are described in U.S. patent application Ser. No. 10/753,614, entitled "Compensated Infrared Absorption Sensor for CO2 and Other Infrared Absorbing Gases", incorporated by reference herein.

Carbon dioxide sensor 202b provides an analog signal, which is periodically updated, such as at 2-second time intervals. To obtain carbon dioxide measurements at concentrations up to about 4 mol % in the test gas, carbon dioxide sensor readings at the 70 psia (low-pressure) test state are used.

Gas outlet port 31 delivers the test gas to valve 207. Temperature sensor 32 provides a temperature output signal to temperature transmitter 205. An example of a suitable temperature sensor 32 is a resistance temperature device. In the example of this description, pressure sensing is accomplished using a pressure port 33 from test chamber 202 in communication with pressure transmitter 204.

Electronics and Communications Module

Referring again to FIG. 1, the sensor outputs from sensor module 200 are routed through pre-processing module 300 to processing module 400. Module 300 may be mounted adjacent to sensor module 200 at the pipeline installation location, and may be in a housing together with one or more of the other modules 200 and 400. Alternatively, module 300 may be remotely connected with appropriate signal communications.

Clock 301 establishes the waveform sampling rate, ultrasonic pulse repetition rate, and other timing control functions used in the waveform averaging process.

Pre-processing unit 302 receives SOS waveform signals from transducer 21 and converts them to digital form. It also accumulates successive waveform traces and forms a repetitive-trace average. The averaged waveform is stored in memory 304 and is available for transfer to processing module 400. Further details of waveform averaging are discussed below in connection with FIGS. 8A-8C. For purposes of this description, a "processor" includes appropriate memory, CPU, and I/O elements for the described function, and may be implemented with appropriate firmware or software or a combination of both.

A/D converter 309 receives the analog temperature, pressure, and CO2 signals from sensor module 200 and converts them to digital form for use in the subsequent inferential gas energy analysis. The pressure and temperature sensor readings, expressed in engineering units (psia and degF), are transferred to the processor 406. The carbon dioxide sensor data, expressed in mol %, are processed through a non-linear compensation unit 402 for nonlinear sensor response at the State 1 test pressure of 70 psia before being transferred to the processor 406. In the example of FIG. 1, the data is also delivered to a sensor monitor 401, whose function is explained below.

Data Acquisition Sequence

Figure 5:
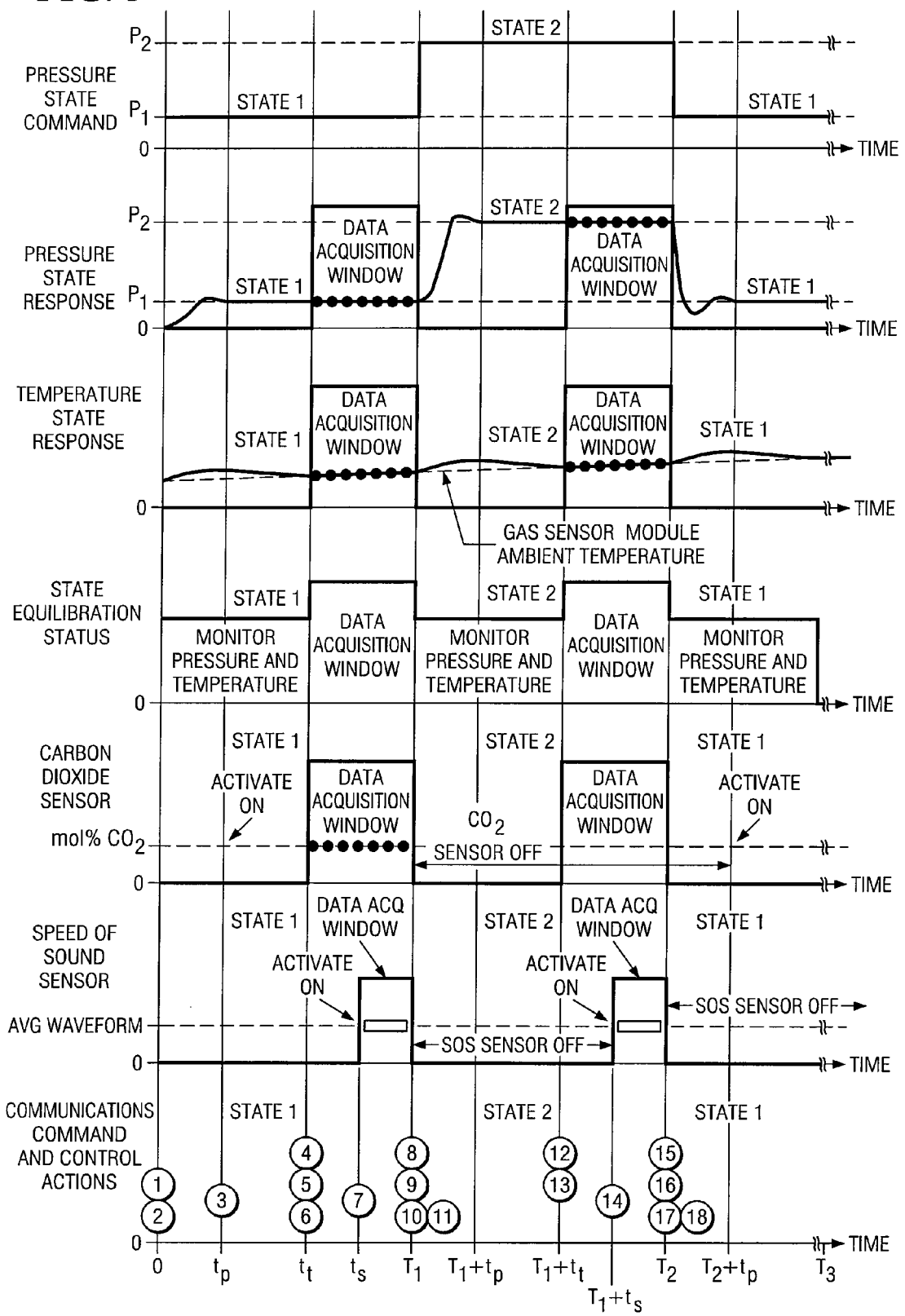
FIG. 5 is a data acquisition and control timing diagram for the system of FIG. 1.

FIG. 5 illustrates the data acquisition sequence performed by sensor module 200 and pre-processing module 300 during a complete two-state gas testing cycle. In the example of this description, processor 406 serve as controller for providing appropriate control signals to appropriate elements of meter 100 as described below.

The initial action in the data acquisition sequence is to command pressure regulator 201b to pressure State 1 and to initiate pressure and temperature monitoring. The gas pressure and temperature in the test chamber 202 undergo transient responses in attaining steady-state conditions in State 1. The pressure stabilization time, $t_p$, is typically in the range of 12-15 seconds for pressures of $P_1$=70 psia and $P_2$=150 psia. The temperature stabilization time, $t_t$, is typically in the range of 20-30 seconds for both pressure states.

CO2 sensor 202b is activated at a time delay of approximately 15 seconds following the State 1 initiation command. This activation step allows CO2 sensor 202b to reach its stabilized response to the CO2 concentration at $P_1$ in advance of recording sensor readings. The pressure and temperature monitoring process during the State 1 stabilization period may be used to determine completion of gas pressure and temperature equilibration and thereby optimally initiate the subsequent data acquisition steps in State 1. Alternately, the subsequent data acquisition steps in State 1 may be initiated after a preset time delay equal to or greater than the longest expected pressure-temperature stabilization time.

Following pressure and temperature stabilization in State 1, a Data Acquisition Window is activated, during which pressure, temperature, and carbon dioxide sensor readings are collected at 2-second time intervals, scaled to engineering units in digital form (psia, degF, and mol %, respectively), and averaged over the duration of the Data Acquisition Window. The calculation of mean and standard deviation values is described in detail below. The State 1 Data Acquisition Window has a preset time duration in the range of 15-20 seconds.

During the second half of the Data Acquisition Window, the SOS sensor 202a is activated at time, $t_s$. At the ultrasonic transmitter pulse repetition rate of 40 pulses/sec, module 300 collects repetitive sound reflection waveforms in A-D converted form and sums these waveforms together in a signal-averaging buffer memory 304.

The signal averaging process may be programmable to provide averaging counts in powers of two ranging from 1 to 256. Adequate signal-to-noise ratios in the ultrasonic waveforms observed in most natural gas mixtures are achieved using an averaging count of 16, requiring a time period of less than one second to acquire.

At the end of the State 1 Data Acquisition Window, processing module 400 requests and receives the averaged waveform in the form of a data file. Processing module 400 then deactivates the CO2 sensor 202b and SOS sensor 202a and commands the pressure regulator 201b to initiate pressure test State 2.

The data acquisition process during State 2 is similar to that in State 1, with the exception that CO2 sensor 202b remains inactive during State 2.

After completing the initial two-state testing cycle, pressure changes between State 1 and State 2 occur as shown at times $T_1$ and $T_2$. Upon completing the data acquisition steps in State 2, processing module 400 commands pressure regulator 201b to initiate pressure test State 1 to begin the next two-state test cycle. The time required to complete the data acquisition sequence for each two-state test cycle is approximately 90 seconds at testing pressures of 70 psia and 150 psia.

The process steps performed during data acquisition are labeled numerically in FIG. 5 as:

1 initiate pressure state 1
2 monitor pressure and temperature
3 activate CO2 sensor
4 record pressure readings
5 record temperature readings
6 record CO2 readings
7 activate SOS sensor
8 record averaged waveform
9 turn off CO2 and SOS sensors
10 initiate pressure state 2
11 monitor pressure and temperature
12 record pressure readings
13 record temperature readings
14 activate SOS sensor
15 record averaged waveform
16 turn off CO2 and SOS sensors
17 initiate pressure state 1
18 continue sequence Data Processing Module Referring again to FIG. 1, processing module 400 may be integrated into the same housing as the other modules 200 and 300 of meter 100. Or module 400 may be a separate unit, remotely connected to pre-processing module 300 via appropriate communications means.

Module 400 has a sensor monitor 401 that receives temperature, pressure, and CO2 readings and monitors data acquisition as described above in connection with FIG. 5. The CO2 data is also delivered to a non-linearity compensator 402, whose operation is described below in connection with FIG. 7. Specific algorithms for data monitoring and CO2 compensation are also described below.

Digital communications interface 403 requests and receives the averaged ultrasonic waveforms stored in memory 304. The waveform files are delivered to the speed of sound processing unit 404, where they are subjected to cross correlation analysis to obtain a normalized correlation function between the two ultrasonic pulse reflections. The sound speed in the gas at each pressure-temperature test state is then calculated by dividing the two-way reflection path distance by the derived time separation (correlation coherence lag time) between the two pulses.

After computing the speed of sound in the test gas for the two test states, these data and the associated pressure, temperature, and carbon dioxide sensor readings are entered into the two-state inferential gas energy processing unit 406, which derives the desired gas properties. Details of the processing performed by processing system 406 are described in further detail below. It is assumed that processor 406 is implemented with appropriate processing, memory, I/O, and peripheral devices, and with appropriate computer programming.

Various additional control functions of processor 406 are to control the sequential operation of the energy meter pressure measurement states (using appropriate signals to pressure regulator 201b, activate the carbon dioxide sensor 202b and speed of sound sensor 202a when required during each pressure state, monitor and record the pressure, temperature, and carbon dioxide sensor readings, and request, receive, and store the ultrasonic waveforms from the speed of sound sensor 202b during each pressure testing state.

A computer interface 407 may be used with the programming of processor 406 to allow energy meter 100 to be interactively programmed to operate at specified pressure-step values, to adjust the data acquisition time intervals, to adjust the speed of sound waveform gain and/or averaging count, and to specify data and diagnostic parameters such as ambient operating temperature, primary power fluctuations, module inert gas purging supply level. Interface 407 may also provide system status data, as well as be used for programming and calibration.

Data Processing Sequence

Figure 6:
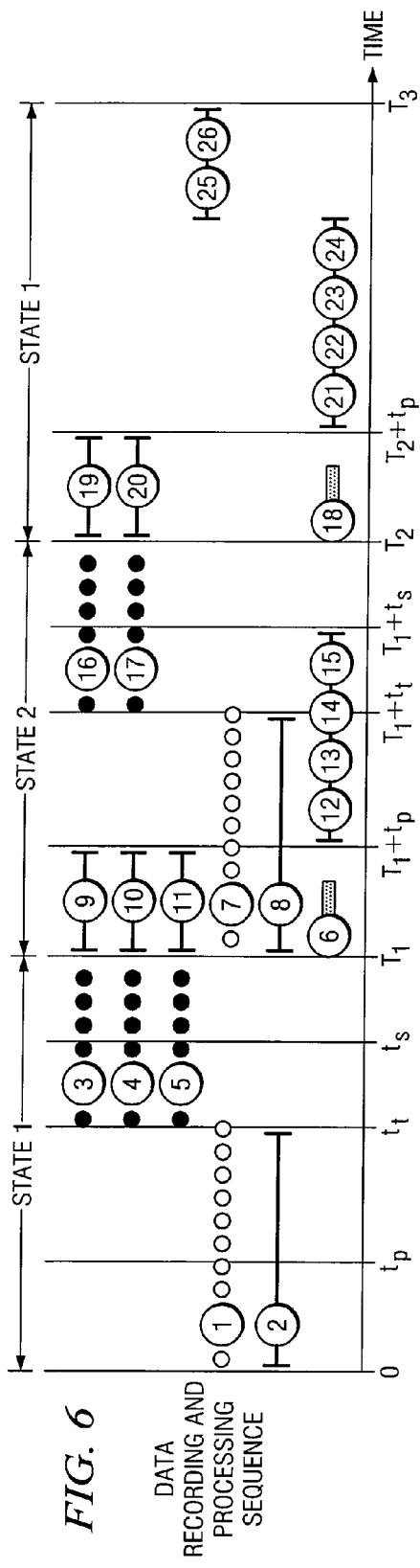
FIG. 6 illustrates the data recording and processing sequence for the system of FIG. 1.

FIG. 6 illustrates various data monitoring, recording, and computational analysis functions, which occur during the two-state cycle. Dots indicate data monitoring in steps 1 and 7, and data recording in steps 3-5 and steps 16 and 17. Solid bars in steps 6 and 18 indicate transfer and recording of ultrasonic waveforms. Computations applied to pressure and temperature stabilization monitoring in State 1 and State 2, indicated by steps 2 and 8, are performed during each state. Computations applied to data recorded during State 1, indicated by steps 9-15, occur during State 2 (after time $T_1$). Computations applied to data recorded during State 2, indicated by steps 19-26, occur during the next State 1 (after time $T_2$).

The specific process steps illustrated in FIG. 6 are:

1 monitor temperature and pressure
2 pressure and temperature stabilization analysis
3 record pressure readings
4 record temperature readings
5 record CO2 readings
6 transfer averaged waveform
7 monitor pressure and temperature
8 pressure and temperature stabilization analysis
9 compute mean pressure and standard deviation
10 compute mean temperature and standard deviation
11 compute mean CO2 and standard deviation
12 compute waveform cross correlation
13 compute correlation lag time interpolation
14 compute speed of sound
15 store computed data
16 record pressure readings
17 record temperature readings
18 transfer averaged waveform
19 compute mean pressure and standard deviation
20 compute mean temperature and standard deviation
21 compute waveform cross correlation
22 compute correlation lag time interpolation
23 compute speed of sound
24 compute gas energy and related parameters
25 store computed data
26 continue sequence The computational operations may be executed by compiled software routines applied to the recorded data files. An example of a suitable programming language is FORTRAN.

The most intensive computations are associated with the waveform cross correlation calculations in steps 13 and 22 and the gas energy analysis in step 24. The computations performed in each test state are expected to be completed within a time period less than the data acquisition and recording sequence in each test state. Computational operations using the data collected during State 1 are performed during data collection in State 2. Similarly, computational operations using data collected during State 2 combined with data collected and analyzed during State 1 are performed after the data acquisition process continues into State 1 of the next two-state testing cycle. Thus, the gas energy analysis in any given two-state testing cycle is completed during the State 1 of the next two-state testing cycle. In the example of this description, the gas energy analysis results for each test cycle will be available within about 135 seconds or less, after initiating each successive two-state test cycle.

The data acquisition and ultrasonic waveform analysis functions described above may be implemented with an advanced "data logging" system having sensor monitoring and data storage capabilities as well as software-driven computational capabilities. This data logger system may serve as master system control for tasks such as: commanding the two test gas pressure changes when required; accepting and numerically analyzing the ultrasonic waveforms and calculating precision speed of sound; applying acquired sensor data and related computed results to the two-state inferential algorithm to derive the gas heating value; and storing the gas heating value and other appropriate data for each measurement cycle to provide long-term monitoring information at natural gas pipeline installation sites. An example of suitable data logging software is the Report Collection System (RCS) Gateway Controller (RGC), available from Integrated Information Technologies, Inc.

Sensor Monitor; Processing Details

Referring again to FIG. 1, sensor monitor 401 stores pressure sensor readings during State 1 as individual variables in a dedicated buffer file. It performs time-running comparisons to determine the time sample point (at 2-sec time intervals) after which changes in pressure are smaller than the resolution tolerance required by the gas energy analysis algorithm, i.e., $\delta P = \pm 0.05$ psi. The criterion used in this process is a mean pressure gradient derived from two time-displaced successive N-point running averages where N typically may be 3-5 sequential sensor readings. A logical comparison of each successive mean pressure gradient value is performed to determine the stabilization time sample at which the pressure change is less than $\pm \delta P$. The pressure condition in State 1 is declared stable when the N-point mean running pressure gradient is less than N times the accuracy tolerance span of the pressure sensor 308. A time flag corresponding to this stability condition may be used to actuate the carbon dioxide sensor 202a during State 1.

The N-point mean running pressure gradient algorithm and logical comparison may be expressed in reduced arithmetic form as:

$$\overline{\Delta P1}_i = |P1_i - P1_{i-N}| < 2N\delta P$$

where $P1_i$=latest pressure sample value in State 1; $P1_{i-N}=N^{th}$ previous pressure sample value in State 1; $\delta P$=magnitude of accuracy tolerance of pressure sensor 308.

The pressure monitoring process in State 2 is similar to that performed in State 1.

Sensor monitor 401 also stores the temperature sensor readings during State 1 as individual variables in a dedicated buffer file for time-running comparisons to determine the time sample point (at 2-sec time intervals) after which changes in temperature are smaller than the resolution tolerance required by the gas energy analysis algorithm, i.e., $\delta T = \pm 0.05$ degF). The criterion used in this process is the mean temperature gradient derived from two time-displaced successive N-point running averages where N typically may be 3-5 sequential sensor readings. A logical comparison of each successive mean temperature gradient value is performed to determine the stabilization time sample at which the temperature change is less than $\pm \delta T$. The temperature stabilization time is generally longer than the pressure stabilization time. The temperature condition in State 1 is declared stable when the N-point mean running temperature gradient is less than N times the accuracy tolerance span of the temperature sensor. A time flag corresponding to this stability condition may be used to actuate the Data Acquisition Window during State 1.

The N-point mean running temperature gradient algorithm may be expressed in reduced arithmetic form as:

$$\overline{\Delta T1}_i = |T1_i - T1_{i-N}| < 2N\delta T,$$

where $T1_i$=latest temperature sample value in State 1; $T1_{i-N}=N^{th}$ previous temperature sample value in State 1; $\delta T$=magnitude of accuracy tolerance of temperature sensor.

The temperature monitoring process in State 2 is similar to that performed for State 1.

Pressure, Temperature, and CO2 Measurement Data Details; Carbon Dioxide Compensation State 1: Upon activating the Data Acquisition Window in State 1, pressure, temperature, and carbon dioxide sensor readings are recorded in dedicated buffer files. Typically, 7 to 10 readings of each parameter will be recorded at 2-second time intervals during State 1. The mean value and the standard deviation value of each measurand are computed and stored, documenting the State 1 measurements. The mean values of these three State 1 parameters will be used later in the gas energy analysis (Step 24 of FIG. 6). The mean and standard deviation values are useful indications of the energy meter system performance and are retained for archive purposes.

The computational formulas for the pressure parameters are:

Mean:

$$\overline{P1} = \frac{1}{NP1}\sum_{n=1}^{NP1} P1_n; n = 1, 2, \ldots, NP1$$

Standard deviation:

$$\sigma_{P1} = \sqrt{\frac{1}{NP1-1}\sum_{n=1}^{NP1}(P1_n - \overline{P1})^2}$$

The computational formulas for the temperature parameters are:

Mean:

$$\overline{T1} = \frac{1}{NT1}\sum_{n=1}^{NT1} T1_n; n = 1, 2, \ldots, NT1$$

Standard deviation:

$$\sigma_{T1} = \sqrt{\frac{1}{NT1-1}\sum_{n=1}^{NT1}(T1_n - \overline{T1})^2}$$

The computational formulas for the carbon dioxide parameters are:
Raw sensor reading:

$$CO_2(raw)_n = \left[\frac{I_{co2} - 4.0}{20.0 - 4.0}\right] \cdot CO_2(FS),$$

where n=1, 2, ..., N.
Preliminary pressure and temperature corrected reading:

$$CO_2(ptc)_n = \left[\frac{T_{abs} + T1}{T_{abs} + T_0}\right] \cdot \left[\frac{P_0}{\overline{P1}}\right] \cdot CO_2(raw); n = 1, 2, \ldots, N$$

Nonlinearity compensated sensor reading:

$$(X_{CO2\_70})_n = \left[A_{70} \cdot \left(\frac{CO_2(ptc)_n}{mol}\right)^3 + B_{70} \cdot \left(\frac{CO_2(ptc)_n}{mol}\right)^2 + C_{70} \cdot \left(\frac{CO_2(ptc)_n}{mol}\right) + D_{70}\right] \cdot (mol \cdot 100),$$

where $A_{70}$=190.561017 $B_{70}$=−11.894645 $C_{70}$=0.666619 $D_{70}$=0.000709661.
Mean:

$$\overline{X_{CO2\_70}} = \frac{1}{N}\sum_{n=1}^{N} X_{CO2\_70_n}; n = 1, 2, \ldots, N$$

Standard deviation:

$$\sigma_{X_{CO2\_70}} = \sqrt{\frac{1}{N-1}\sum_{n=1}^{N}(X_{CO2\_70_n} - \overline{X_{CO2\_70}})^2},$$

where $I_{CO2}$=analog current reading of carbon dioxide sensor; $CO_2(FS)$=full-scale measurement range of carbon dioxide sensor (mol %); $T_{abs}$=459.67R; $T_o$=77.0 degF=sensor calibration reference temperature; $P_o$=14.73 psia=sensor calibration reference pressure; $\overline{P1}$=70 psia=mean gas test pressure in State 1; and $A_{70}$, $B_{70}$, $C_{70}$, $D_{70}$=regression coefficients for third-degree polynomial compensation of carbon dioxide sensor nonlinearity at $\overline{P1}$=70 psia in State 1.

Figure 7:
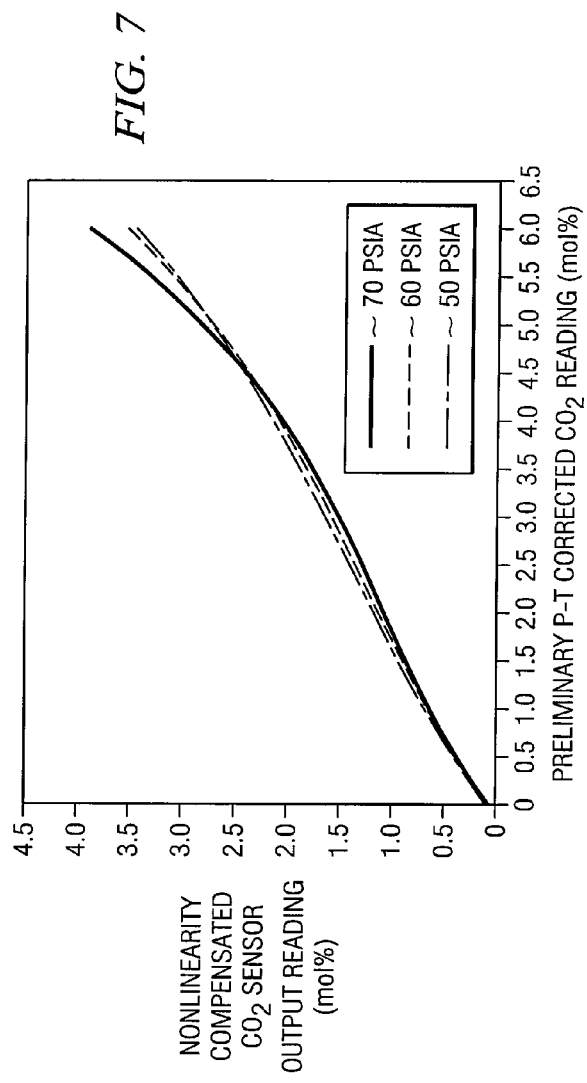
FIG. 7 is a chart illustrating carbon dioxide nonlinearity compensation.

FIG. 7 is a carbon dioxide nonlinearity compensation chart, which illustrates the nonlinearity between the pressure-temperature corrected sensor reading and the true carbon dioxide concentration in the tested gas at a mean pressure of $\overline{P1}$=70 psia. As shown in FIG. 7, the nonlinearity is slightly dependent on the gas testing pressure. For actual mean test pressures within $\overline{P1}$=70±2 psia, an empirical pressure correction factor can be applied to the compensated carbon dioxide reading at $\overline{P1}$=70 psia indicated in the above equation without modifying the regression coefficients stated above. That is, the pressure-adjusted nonlinearity-compensated value of carbon dioxide concentration is:

$$(X_{CO2\_\overline{P1}})_n = \left[\frac{70.0\ psia}{\overline{P1}}\right]^q \cdot (X_{CO2\_70})_n$$

where q≅0.2; 68 psia<$\overline{P1}$<72 psia.

State 2: Upon activating the Data Acquisition Window in State 2, pressure and temperature sensor readings are recorded in dedicated buffer files. Typically, 7 to 10 readings of each parameter will be recorded at 2-second time intervals during State 2. The mean value and the standard deviation value of each measurand is computed and stored in a permanent data file documenting the State 2 measurements. The mean values of these two State 2 parameters will be used later in the gas energy analysis (Step 24 of FIG. 6). The mean and standard deviation values are useful indications of the energy meter system performance and are retained for archive purposes.

The computational formulas for the pressure parameters are:
Mean:

$$\overline{P2} = \frac{1}{NP2}\sum_{n=1}^{NP2} P2_n; n = 1, 2, \ldots, NP2$$

Standard deviation:

$$\sigma_{P2} = \sqrt{\frac{1}{NP2-1}\sum_{n=1}^{NP2}(P2_n - \overline{P2})^2}.$$

The computational formulas for the temperature parameters are:
Mean:

$$\overline{T2} = \frac{1}{NT2}\sum_{n=1}^{NT2} T2_n; n = 1, 2, \ldots, NT2$$

Standard deviation:

$$\sigma_{T2} = \sqrt{\frac{1}{NT2-1}\sum_{n=1}^{NT2}(T2_n - \overline{T2})^2}.$$

No carbon dioxide sensor readings are recorded or processed for the test conditions in State 2.

Speed of Sound Processing Details

The averaged ultrasonic waveforms transferred to processing module 400 from SOS pre-processor 302 at the end of State 1 and State 2 are discrete-time signals each containing an early-time reflection wavelet and a later-time reflection wavelet.

Figure 8A:
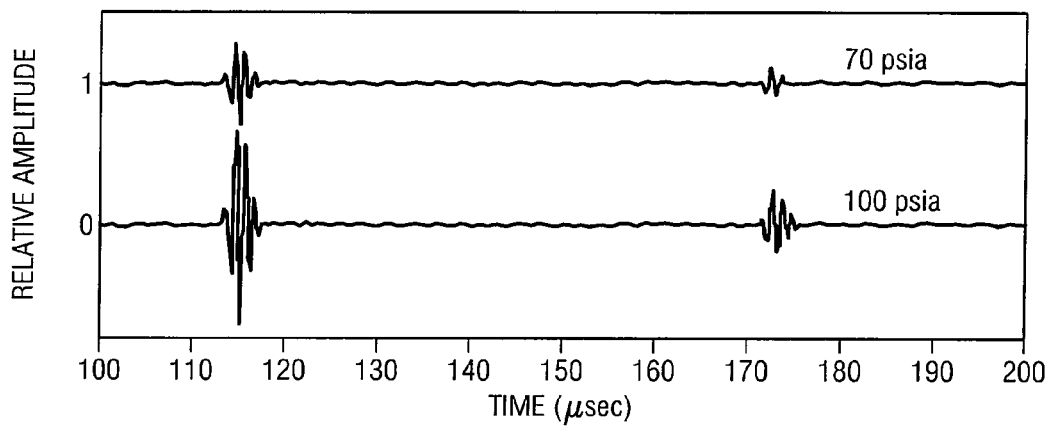
FIGS. 8A-8C illustrate the reflection waveforms generated by the speed of sound sensor of FIGS. 1, 2, and 3.
Figure 8B:
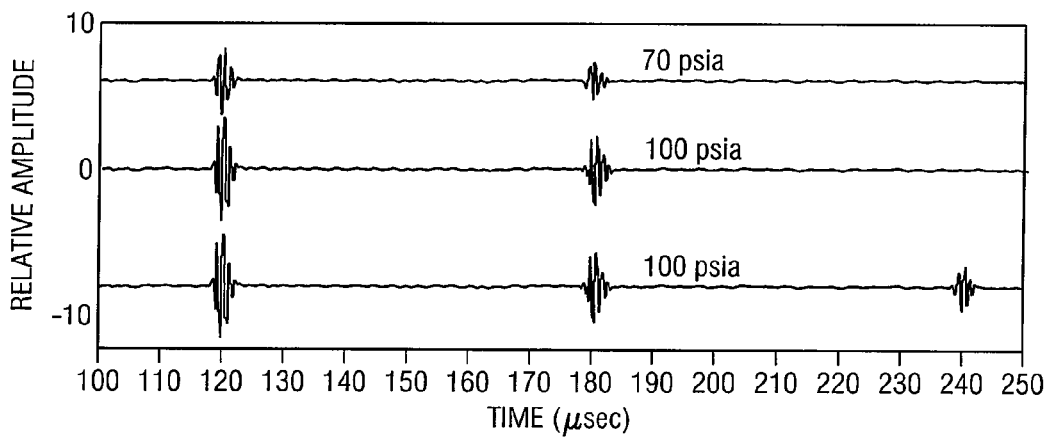
Figure 8C:
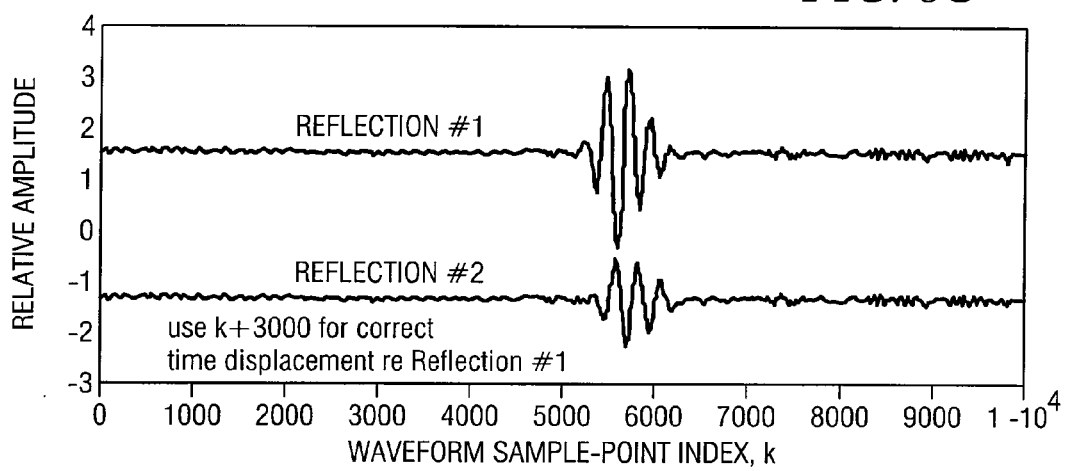

FIGS. 8A-8C illustrate examples of ultrasonic pulse-echo waveforms provided by a 1 MHz transducer 21 excited by a 200-Vpk impulse. The waveforms represent the ultrasonic signals after conversion to 12-bit digital form at a sampling rate of 50 MSamples/sec and stored in 10,000-word trace files in memory 304.

The traces in FIGS. 8A and 8B show the complete waveforms for two different gases at two different pressure states. The reflection wavelets are separated by a time difference of approximately $\Delta T \cong 60$ μsec.

In FIG. 8A, signal averaging of 64 waveforms were used to improve the signal-to-noise ratio of the second reflection. In the lower trace, the higher gas density at 100 psia improves the acoustic coupling and the observed signal strength.

The traces in FIG. 8B were recorded in a test gas having a higher density and lower absorptive attenuation than that of the test gas of FIG. 8A. Signal averaging of 64 traces is more than adequate to provide good signal-to-noise ratios in this test gas. The bottom trace in FIG. 8B, recorded at one-half the sampling rate, shows the later arrival of a secondary reflection at a time equal to twice that of the first reflection, indicating that it is the first multiple reflection between the transducer and the first reflector face.

The traces in FIG. 8C are separated shorter-time-base recordings of the first and second reflections for the test gas of FIG. 8B, at 70 psia. This illustrates their wavelet details and typical noise contamination remaining after averaging eight repetitive traces. The second reflection has lower amplitude than the first reflection because of absorptive attenuation effects in the gas in the operating frequency range of 800-1200 kHz.

The physical path length between the two reflection faces of target 23 is known and invariant. Thus, the travel time difference between the two reflections is a measure of the speed of sound in the gas at the measured pressure and temperature conditions in the test chamber 202. At constant temperature, the speed of sound in natural gas decreases with increasing pressure in the pressure range used in the State 1 and State 2 tests. Because the speed of sound in the gas at State 1 conditions is different from the speed of sound at State 2 conditions, the time differences between the reflection wavelets are also different.

For typical natural gas compositions at testing pressures of P1=70 psia and P2=150 psia over a range of ambient temperatures and for a known target separation distance of 1 inch, the two-way reflection time differences are bounded in the range of approximately 55 μsec<$\Delta T$<65 μsec. Thus, a cross correlation function between the first and second reflection wavelets may be obtained by computing an "autocorrelation" function, using a correlation lag-time window defined by $0 \leq \tau \leq 65$ μsec, where τ is a correlation time-lag parameter.

U.S. patent application Ser. No. 10/894,084, entitled "Correlation Method for Use with Speed of Sound Sensor", incorporated by reference herein, describes a time-domain implementation of the autocorrelation function. This procedure is preferred when the cross correlation analysis is implemented in a microprocessor operating under firmware program execution.

When the cross correlation analysis is implemented in a compiled software code, the preferred computing procedure is one involving the Fourier transforms of the time-windowed reflection wavelets. This process involves computing the Fourier transforms of the two windowed reflection signals, multiplying one transform by the complex conjugate of the other transform to obtain the cross spectral density, and computing the inverse transform to obtain the cross correlation function in the time domain. This time domain result will indicate the wavelet coherence time lag associated with the windowed reflections. The total time lag is then calculated as the sum of lag time derived from the windowed reflection signals and the time separation between the two time windows.

U.S. patent application Ser. No. 10/894,084 further describes a statistically determined interpolation of the time shift, obtained by fitting a second-degree polynomial, i.e., a parabola, to the sample points comprising the positive lobe of the cross correlation function.

Various factors may cause errors in the SOS value. Because stored values of the sampling rate and the distance between the target reflectors are used in computing the speed of sound, either one of these stored values may be adjusted to serve as a basis for speed of sound calibration.

Accurate values of sound speed in known natural gas mixtures at a known pressure and temperature state may be calculated using a thermodynamic equation of state such as that currently designated by the gas industry as AGA-10. The speed of sound sensor 202a may, therefore, be calibrated by temporarily introducing a certified natural gas mixture into the test chamber and experimentally deriving its speed of sound at measured values of pressure and temperature using a measured value of the distance between the reflection targets. The true speed of sound in the certified mixture is then calculated at the same pressure and temperature. The ratio of the calculated and reference sound speeds may then serve as a calibration adjustment factor for the sensor-derived speed of sound.

Inferential Gas Property Analysis Details

As stated above, the inferential gas property analysis is performed by processor 406. It uses temperature, pressure, CO2, and speed of sound data to inferentially determine various gas properties. Typical properties so derived are the standard volumetric heating value and the nitrogen concentration of the test gas. These two quantities together with the carbon dioxide concentration form the principal gas monitoring information determined by the two-state gas energy measurement method. Other useful gas parameters may also be derived from the same data and from associated interim algorithm results, including gas total molecular weight, standard gas density, gas compressibility, speed of sound at standard conditions, and date/time of data acquisition.

Details regarding the two-state inferential algorithms implemented by programming of processing unit 406 are described in U.S. Pat. Nos. 6,604,051 and 6,704,660, 6,850, 847, and 6,804,610, referenced in the Background and incorporated by reference herein.

Essentially, the process involves accessing a set of reference speed of sound and density values, derived from a set of reference gas mixtures, at least some of the gas mixtures containing diluents, at the known temperature and pressure. The desired property of the gas mixture, for example density, is modeled as a function of its speed of sound, a number of coefficients, and its concentration of diluents, thereby obtaining a model equation. The reference speed of sound and reference density values are used to determine values for the coefficients.

Appropriate sensors and pre-processing devices, such as those described above, are used to acquire values for CO2, temperature, and pressure. Speed of sound values are acquired at two different states of the gas. The coefficient values and acquired values for the speed of sound, CO2, temperature, and pressure are substituted into the model equation. The model equation is solved at the two different temperature/pressure states to determine both the nitrogen concentration value and the desired property of the gas mixture.

What is claimed is:

1. A gas meter that determines one or more properties of a gas mixture, using an inferential algorithm, comprising:

a gas sensor module having: a pressure regulator for receiving the gas mixture and for regulating the pressure of the gas mixture; a test chamber for receiving an amount of pressure-regulated gas mixture, for testing the gas to provide a waveform output signal from which the speed of sound in the gas mixture can be derived, and for providing an output signal representing the carbon dioxide concentration of the gas mixture; a temperature sensor for providing a signal representing the temperature of the gas mixture in the test chamber; a pressure sensor for providing a signal representing the pressure of the gas in the test chamber; and a release valve for controlling the release of the gas from test chamber;

wherein the pressure regulator is controllable to provide two pressure states of the gas in the test chamber;

wherein the test chamber has a speed of sound sensing channel for containing a first portion of the gas mixture during speed of sound testing, a carbon dioxide sensing subchamber for containing a second portion of the gas mixture during carbon dioxide measurement, and a closed internal conduit that provides a defined linear passageway between the speed of sound sensing channel and the carbon dioxide sensing subchamber, such that the first portion and second portion are in fluid communication via the conduit;

a pre-processing module for receiving the output signals from the sensor module signals and for providing data representing each of these signals; thereby providing temperature data, pressure data, speed of sound data, and carbon dioxide data; and a processing module for using the speed of sound data to calculate the speed of sound in the gas, and to use the temperature, pressure, carbon dioxide, and speed of sound data at two states of the gas to inferentially determine at least one property of the gas mixture.

2. The meter of claim 1, wherein the meter determines one or more of the gas properties: heating content, density, molecular weight.

3. The meter of claim 1, wherein the test chamber provides the waveform output signal by using a transducer that transmits an acoustic signal to a dual target reflector and receives a reflected waveform having two reflection wavelets.

4. The meter of claim 1, wherein the transducer is an ultrasonic transducer.

5. The meter of claim 1, wherein at least a portion of the test chamber is surrounded by a helical flow channel for carrying the gas around the test chamber, such that the gas attains the temperature of the test chamber.

6. The meter of claim 1, wherein the test chamber is sealed during a first pressure state and a second pressure state, such that the waveform may be provided at two pressure states.

7. The meter of claim 1, wherein the sensor module is remote from the pre-processing module, and further comprising a transmitter for transmitting at least one of the output signals from the sensor module to the pre-processing module.

8. The meter of claim 1, wherein the sensor module is housed in the same housing with the pre-processor module.

9. The meter of claim 1, wherein the sensor module is housed in the same housing with the pre-processor module and the processing module.

10. The meter of claim 1, wherein the sensor module is operable to be placed in situ in a gas pipeline.

11. The meter of claim 1, wherein the sensor module is operable to receive a portion of gas from a gas pipeline.

12. The meter of claim 1, wherein the sensor module has an infrared sensor for providing the carbon dioxide output signal.

13. The meter of claim 1, wherein the pre-processor module further comprises a device for transmitting and receiving acoustic waveforms to and from the test chamber.

14. The meter of claim 1, further comprising a speed of sound waveform pre-processor for averaging speed of sound waveforms.

15. The meter of claim 1, further comprising a sensor monitor for determining when temperature and/or pressure in the test chamber is stable.

16. The meter of claim 1, further comprising a controller for controlling acquisition of output signals from the test chamber during at least two pressure states of the gas mixture in the test chamber.

17. The meter of claim 1, further comprising a speed of sound data processor for receiving the speed of sound data from the pre-processing module, for using the data to calculate the time delay between reflections in the speed of sound waveform, and for delivering time delay data to the processing module.

18. The meter of claim 1, wherein the test chamber is sealable to maintain the gas mixture at a uniform pressure state during testing of the gas for both speed of sound and carbon dioxide concentration.

19. The meter of claim 5, wherein the helical flow channel is operable as a heat sink to equilibrate the temperature of gas into the test chamber to the temperature of the test chamber before the gas enters the speed of sound measurement channel.

* * * * *